(12) United States Patent
Pop et al.

(10) Patent No.: US 10,709,372 B2
(45) Date of Patent: Jul. 14, 2020

(54) SYSTEM FOR MONITORING INCONTINENCE

(71) Applicant: Stichting IMEC Nederland, Eindhoven (NL)

(72) Inventors: Valer Pop, Eindhoven (NL); Salvatore Polito, Einhoven (NL)

(73) Assignee: STICHTING IMEC NEDERLAND, Eindhoven (NL)

( * ) Notice: Subject to any disclaimer, the term of this patent is extended or adjusted under 35 U.S.C. 154(b) by 0 days.

(21) Appl. No.: 16/217,384

(22) Filed: Dec. 12, 2018

(65) Prior Publication Data

US 2019/0110730 A1   Apr. 18, 2019

Related U.S. Application Data

(63) Continuation of application No. 14/532,207, filed on Nov. 4, 2014, now abandoned.

(51) Int. Cl.
*A61B 5/20* (2006.01)
*A61B 5/11* (2006.01)
(Continued)

(52) U.S. Cl.
CPC .............. *A61B 5/204* (2013.01); *A61B 5/076* (2013.01); *A61B 5/1116* (2013.01); *A61B 5/686* (2013.01);
(Continued)

(58) Field of Classification Search
CPC ..... A61B 5/204; A61B 5/208; A61B 5/14507; A61F 13/42
See application file for complete search history.

(56) References Cited

U.S. PATENT DOCUMENTS

| 5,103,835 | A | 4/1992 | Yamada et al. |
| 5,704,353 | A | 1/1998 | Kalb et al. |

(Continued)

FOREIGN PATENT DOCUMENTS

| CN | 103126672 | 6/2013 |
| DE | 102011108252 A1 | 1/2013 |

(Continued)

OTHER PUBLICATIONS

Final Office Action dated Jun. 29, 2018 from the USPTO in U.S. Appl. No. 14/532,216.

(Continued)

*Primary Examiner* — Carl H Layno
*Assistant Examiner* — Dacheng Xie
(74) *Attorney, Agent, or Firm* — Dilworth IP, LLC (57) ABSTRACT

According to one aspect of the inventive concept there is provided a system for monitoring incontinence comprising: a urine sensitive circuit arranged to present a changed electrical characteristic when exposed to urine; a measurement circuit arranged to perform a measurement on a urine bladder of a wearer to determine at least one parameter which varies with a fill level of the urine bladder; a sensor arranged to determine an orientation and/or a movement of the sensor; and a processing circuit arranged to: determine whether the urine sensitive circuit has been exposed to urine; estimate an amount of urine released on to the urine sensitive circuit; and in response to determining that the urine sensitive circuit has been exposed to urine, record data representing said at least one parameter determined by the measurement circuit, an estimated movement and/or posture of the wearer based on an orientation and/or a movement determined by the sensor, and an estimate of the amount of urine released on to the urine sensitive circuit.

20 Claims, 2 Drawing Sheets

(51) Int. Cl.
   *A61B 5/07* (2006.01)
   *A61B 5/00* (2006.01)
   *A61B 5/1473* (2006.01)
   *A61B 5/145* (2006.01)

(52) U.S. Cl.
   CPC .......... *A61B 5/6885* (2013.01); *A61B 5/1473* (2013.01); *A61B 5/14507* (2013.01); *A61B 2562/0219* (2013.01)

(56) References Cited

U.S. PATENT DOCUMENTS

| | | | |
|---|---|---|---|
| 5,959,535 | A | 9/1999 | Remsburg |
| 5,964,710 | A | 10/1999 | Ganguly et al. |
| 6,359,190 | B1 | 3/2002 | Ter-Ovanesyan |
| 9,327,117 | B2 | 5/2016 | Denison et al. |
| 2007/0027494 | A1 | 2/2007 | Gerber |
| 2007/0252713 | A1 | 11/2007 | Rondoni et al. |
| 2007/0255176 | A1 | 11/2007 | Rondoni et al. |
| 2008/0058680 | A1 | 3/2008 | Lee et al. |
| 2008/0266117 | A1 | 10/2008 | Song et al. |
| 2008/0300651 | A1 | 12/2008 | Gerber et al. |
| 2009/0315720 | A1 | 12/2009 | Clement et al. |
| 2010/0121161 | A1 | 5/2010 | Robertson |
| 2010/0168702 | A1 | 7/2010 | Ales, III et al. |
| 2010/0217148 | A1 | 8/2010 | Binder |
| 2010/0280397 | A1 | 11/2010 | Feldman et al. |
| 2012/0035496 | A1 | 2/2012 | Denison et al. |
| 2012/0119920 | A1 | 5/2012 | Sallop et al. |
| 2012/0197336 | A1* | 8/2012 | Su ............... A61N 1/36007 607/41 |
| 2013/0012896 | A1 | 1/2013 | Suzuki et al. |
| 2014/0018636 | A1* | 1/2014 | Contant .............. G06F 19/3475 600/301 |
| 2014/0142549 | A1 | 5/2014 | Su et al. |
| 2014/0200538 | A1* | 7/2014 | Euliano ................ A61F 13/42 604/361 |
| 2015/0076000 | A1 | 3/2015 | Ehrensberger et al. |
| 2016/0120453 | A1 | 5/2016 | Pop et al. |
| 2016/0120455 | A1 | 5/2016 | Pop et al. |

FOREIGN PATENT DOCUMENTS

| | | | |
|---|---|---|---|
| EP | 1731101 | A1 | 12/2006 |
| EP | 2019995 | A1 | 2/2009 |
| JP | H05137704 | A | 6/1993 |
| JP | H05245169 | A | 9/1993 |
| JP | H07239990 | A | 9/1995 |
| JP | H0880285 | A | 3/1996 |
| JP | S63252138 | A | 10/1998 |
| JP | 2002224093 | A | 8/2002 |
| JP | 2002224093 | A1 | 8/2003 |
| JP | 2011147505 | A | 8/2011 |
| JP | 2011-078791 | A | 11/2012 |
| JP | 2013-039158 | A | 2/2013 |
| JP | 2013039158 | A | 2/2013 |
| JP | 2013509280 | A | 3/2013 |
| JP | 2013094175 | A | 5/2013 |
| JP | 2013-523305 | A1 | 6/2013 |
| JP | 2013523305 | A | 6/2013 |
| JP | 2013132518 | A | 7/2013 |
| JP | 2014023813 | A | 2/2014 |
| JP | 2014527623 | A | 10/2014 |
| JP | 6339480 | B2 | 6/2018 |
| WO | 0000082 | A1 | 1/2000 |
| WO | 2005/099582 | A1 | 10/2005 |
| WO | 2005099582 | A1 | 10/2005 |
| WO | 2009060448 | A2 | 5/2009 |
| WO | 2011125003 | A1 | 10/2011 |
| WO | 2013013782 | A2 | 1/2013 |
| WO | 2013016765 | A1 | 2/2013 |
| WO | 2013023054 | A2 | 2/2013 |
| WO | 2013076593 | A1 | 5/2013 |
| WO | 2013095230 | | 6/2013 |
| WO | 2014067248 | A1 | 5/2014 |
| WO | 2014087343 | A1 | 6/2014 |

OTHER PUBLICATIONS

Non-Final Office Action dated Dec. 14, 2016 issued by the USPTO in U.S. Appl. No. 14/532,225.
Final Office Action dated Dec. 16, 2016 issued by the USPTO in U.S. Appl. No. 14/532,216.
Non-Final Office Action dated Mar. 18, 2016 issued by the USPTO in U.S. Appl. No. 14/532,216.
Office Action dated Sep. 26, 2017 issued by the Japanese Patent Office in JP Patent Application No. 2014-224037 along with unofficial English translation.
Office Action dated Oct. 31, 2017 issued by the Japanese Patent Office in JP Patent Application No. 2014-224038 along with unofficial English translation.
Office Action dated Sep. 19, 2017 issued by the Japanese Patent Office in JP Patent Application No. 2014-224039 along with unofficial English translation.
Examination Report dated Sep. 14, 2017 from the Australian Patent Office in AU Patent Application No. 2014259488.
Final Office Action dated Oct. 3, 2017 from the USPTO in U.S. Appl. No. 14/532,225.
Kim et al., Bladder Volume Measurement, vol. 77, No. 6, Nov./Dec. 1998, pp. 498-502.
Non-Final Office Action dated Oct. 4, 2017 from the USPTO in U.S. Appl. No. 14/532,216.
Non-Final Office Action dated Sep. 26, 2018 from the USPTO in U.S. Appl. No. 14/532,225.
Search Report and Written Opinion mailed in Netherlands Patent Application 2013740 dated Jun. 16, 2015.
U.S. Appl. No. 16/217,430, filed Dec. 12, 2018.
Australian Examination Report, Application No. 2014259486, dated Jul. 9, 2018, 10 pages.
JPO Notification of Reasons for Rejection, Application No. 2014 224037, dated May 22, 2018, 14 pages.
Non-Final Office Action dated Oct. 17, 2019 issued by the USPTO in U.S. Appl. No. 16/217,430.
Notice of Reasons for Refusal from JPO; Application No. JP 2018-219850, dated Oct. 8, 2019, 10 pages.

* cited by examiner

SYSTEM FOR MONITORING INCONTINENCE

This application claims the benefit of U.S. patent application Ser. No. 14/532,207, filed Nov. 4, 2014, now Abandoned, the disclosure of which is hereby incorporated herein by reference in its entirety.

TECHNICAL FIELD

The present inventive concept relates to a system for monitoring incontinence.

BACKGROUND

Urinary incontinence, or an inability to control urinary function, is a common problem affecting both men and women of all ages. Many feel embarrassed and do not dare to visit the doctor for help. This can lead to chronic incontinence. In the prior art, a common way of managing incontinence is to use absorbent articles such as diapers, sanitary napkins or pads, or even catheters. However, this only reduces the inconvenience for a wearer when an incontinence event occurs.

Common types of urinary incontinence include stress incontinence and urge incontinence. There is also a mixed type of incontinence including both stress incontinence and urge incontinence. Stress incontinence may be caused by loss of support of the urethra which is usually a consequence of damage to pelvic support structures as a result of childbirth, overweight or and some medications. Stress incontinence is typically characterized by a leakage of a relatively small volume of urine during activities which increase abdominal pressure such as coughing, sneezing and lifting, or rapid movements for example during sporting activities. The main treatment for stress incontinence is pelvic floor exercises. Other possibilities would be a surgery to tighten or support the bladder outlet or prescription of medications. Urge incontinence may on the other hand be caused by abnormal bladder contractions. This is sometimes also referred to as an "overactive" urine bladder. Urge incontinence is typically characterized by a leakage of a relatively large volume of urine in association with insufficient warning to get to the bathroom in time. Possible treatments for urge incontinence are pelvic floor exercises to retrain the bladder or prescription of medications to relax the bladder.

In the prior art, various systems relying on electrical sensors for detecting presence or urine in for example a diaper are known. Such prior art systems are however often merely able to detect that the diaper has become wet and signal the need to change the diaper to for example the wearer of the diaper or a caretaker. However, this only provides a limited help to people suffering from incontinence in that it mainly make it easier for the wearer or caretaker to determine that it may be time to change the diaper.

SUMMARY OF THE INVENTIVE CONCEPT

The inventors have realized that it would be advantageous to provide a system allowing for an improved monitoring of urinary incontinence. More specifically the inventors have realized that, for a great number of people suffering from incontinence-like problems, it would be helpful to have a system for monitoring incontinence providing monitoring of aspects other than merely the need to change diaper.

According to an aspect of the present inventive concept there is provided a system for monitoring incontinence comprising:
- a urine sensitive circuit arranged to present a changed electrical characteristic when exposed to urine;
- a measurement circuit arranged to perform a measurement on a urine bladder of a wearer to determine at least one parameter which varies with a fill level of the urine bladder;
- a sensor arranged to determine an orientation and/or a movement of the sensor; and
- a processing circuit arranged to:
    - determine whether the urine sensitive circuit has been exposed to urine,
    - estimate an amount of urine released on to the urine sensitive circuit, and
    - in response to determining that the urine sensitive circuit has been exposed to urine, record data representing said at least one parameter determined by the measurement circuit, an estimated movement and/or posture of the wearer based on an orientation and/or a movement determined by the sensor, and an estimate of the amount of urine released on to the urine sensitive circuit.

The system makes it possible to correlate an actual detection of an involuntary urination event (hereinafter interchangeably referred to as a urination event or an incontinence event) with a parameter which is indicative of a urine bladder fill level, an estimated movement and/or posture of the wearer (which is indicative of a current activity of the wearer) as well as an estimation of an amount of urine released by the wearer. This type of correlation may be particularly useful for monitoring stress incontinence which, as described earlier, typically is characterized by a leakage of a relatively small volume of urine during activities which increase abdominal pressure. Information regarding a fill level of the urine bladder, a movement/posture and the amount or urine released may thereby be valuable for understanding which activities may cause incontinence, and the severity of the incontinence in those activities. However, it should also be noted that the system also may be useful for monitoring urge and mixed-type incontinence.

By triggering the recording of the data in response to detecting or determining that the urine sensitive circuit has been exposed to urine, an accurate monitoring is provided since the urine bladder fill level indicative parameter, as well as the estimated movement and/or posture of the wearer will correspond to the conditions prevailing at the time of the incontinence event. This accuracy would be difficult to achieve with any manual monitoring method.

According to one embodiment the processing circuit is further arranged to, in response to determining that the urine sensitive circuit has been exposed to urine, record an association between said at least one parameter determined by the measurement circuit, the estimated movement and/or posture and the estimate of the amount of urine released on to the urine sensitive circuit. In other words, the processing circuit is arranged to logically link said at least one parameter determined by the measurement circuit, the estimated movement/posture and the estimate of the amount of urine released on to the urine sensitive circuit.

The processing circuit may further be arranged to record in said data, an indication of that the urine sensitive circuit has been exposed to urine. The processing circuit may hence be arranged to associate the indication of that the urine sensitive circuit has been exposed to urine with (or link the indication of that the urine sensitive circuit has been exposed to urine to) said at least one parameter determined by the measurement circuit, the estimated movement/posture and the estimate of the amount of urine released on to the urine sensitive circuit.

The processing circuit may be arranged to record the data in a memory.

According to one embodiment the processing circuit is arranged to determine that the urine sensitive circuit has been exposed to urine based on the changed electrical characteristic. More specifically, the processing circuit may determine that the urine sensitive circuit has been exposed to urine by detecting the changed electrical characteristic of the urine sensitive circuit.

According to one embodiment the urine sensitive circuit is arranged to present an electrical response when exposed to urine, and wherein the processing circuit is arranged to determine that the urine sensitive circuit has been exposed to urine by detecting the electrical response of the urine sensitive circuit.

According to one embodiment the changed electrical characteristic of the urine sensitive circuit is indicative of/proportional to the amount of urine released on to the urine sensitive circuit.

According to one embodiment the electrical response of the urine sensitive circuit is indicative of/proportional to the amount of urine released on to the urine sensitive circuit, and wherein the processing circuit is arranged to estimate the amount of urine released on to the urine sensitive circuit based on the electrical response of the urine sensitive circuit.

According to one embodiment the changed electrical characteristic or the electrical response of the urine sensitive circuit includes one or more selected from the group comprising: a changed resistance, a changed capacitance, a changed inductance, a changed impedance, a changed resonance frequency, a changed voltage generated by the urine sensitive circuit, a changed current generated by the urine sensitive circuit, a changed resonance frequency of the urine sensitive circuit.

According to one embodiment the processing circuit is arranged to estimate the amount of urine released on to the urine sensitive circuit by determining a size of the change.

According to one embodiment the urine sensitive circuit includes a portion arranged to generate a current when exposed to urine to power a transmission of a signal from the urine sensitive circuit, and wherein the processing circuit is arranged to record said data in response to receiving the signal from the urine sensitive circuit. Thus, the urination event may directly trigger the recording of the data by the processing circuit. Moreover, since the current powering the transmission of the signal is generated by the urine, no additional power source in the urine sensitive circuit is required. The urine sensitive circuit may thereby be produced rationally at a relatively low cost.

According to one embodiment the signal transmitted from the urine sensitive circuit is indicative of the amount of urine released on to the urine sensitive circuit, and wherein the processing circuit is arranged to estimate the amount of urine released on to the urine sensitive circuit based on the signal received from the urine sensitive circuit.

According to one embodiment the current generated by the portion is proportional to a surface area of the portion being exposed to urine.

According to one embodiment the portion includes a first conducting path or electrode arranged to act as an anode and a second conducting path or electrode arranged to act as a cathode when the portion is exposed to urine. An anode-cathode pair makes rational and relatively inexpensive production of a reliable, self-powered urine sensitive circuit possible.

According to one embodiment the urine sensitive circuit portion includes a portion arranged to generate a current when exposed to urine for powering an increment of a counter stored in a memory of the urine sensitive circuit. Information regarding the amount of moisture resulting from a plurality of subsequent urinations may thereby be collected with a reduced amount of signaling between the processing circuit and the urine sensitive circuit.

Accordingly, the processing circuit may be arranged to estimate the amount of urine released on to the urine sensitive circuit based on the counter.

According to one embodiment the processing circuit is further arranged to, in response to determining that the urine sensitive circuit has been exposed to urine, record time data. The time of the incontinence event may thereby be recorded.

According to one embodiment the processing circuit is further arranged to estimate a urine bladder fill level based on the at least one determined parameter, i.e. by using the at least one determined parameter. The estimate of the urine bladder fill level may be included in said recorded data.

According to one embodiment the processing circuit is arranged to provide a signal which is indicative of a urine bladder fill level based on the determined parameter. The signal may for example be used to provide a user with information on the bladder fill level. The signal may indicate the fill level in relative or absolute terms. A user of the system may, based on this information, be able to decide whether it is time to visit the toilet or not.

According to one embodiment the processing circuit is arranged to provide an alarm signal in response to determining that the urine sensitive circuit has been exposed to urine. A user may thus be informed of that a urine leakage has occurred, which otherwise could have passed by unnoticed. This may simplify for the user to understand which situations may lead to involuntary urination.

According to one embodiment the system further comprises at least one or a combination of a microphone, a temperature sensor, an accelerometer or an altimeter. Further sensors enable more parameters which may have an influence on the urination event to be recorded in the data. Thus, parameters measured by these sensors may be included in the data recorded by the processing circuit in response to a urination event.

According to one embodiment the measurement circuit and the processing circuit are galvanically connected. This may enable a simple communication between the measurement circuit and processing circuit.

According to one embodiment the processing circuit and the urine sensitive circuit are galvanically separated. This may simplify use of the system since the urine sensitive circuit may be handled without having to deal with any wiring. Also, it allows the urine sensitive circuit to be used as a disposable component of the system which easily may be replaced following an incontinence event.

According to one embodiment the measurement circuit is arranged to measure an impedance of the urine bladder, and/or perform an ultrasound measurement of a dimension of the urine bladder. These types of measurements may enable an accurate estimation of the urine bladder fillness level.

According to one embodiment the processing circuit is further arranged to determine a threshold based on the at least one determined parameter represented by the recorded data. A threshold corresponding to a urine bladder fill threshold may thus be determined. Since the threshold is based on the at least one determined parameter the threshold may be determined to correspond to a fill level of the urine bladder at, and above, which there is an increased risk for an incontinence event. Moreover by basing the threshold on the at least one determined parameter, which is/are measured parameter(s), the threshold may be tailored for a specific individual.

According to one embodiment the processing circuit is further arranged to determine a threshold based on the at least one determined parameter represented by the recorded data and a previously determined threshold. The advantages discussed in connection with the preceding embodiment applies correspondingly to this embodiment. Moreover by basing the threshold determination also on a previously determined threshold, the threshold may over time be tuned to better correspond to the incontinence problems for the specific individual.

According to one embodiment the processing circuit is further arranged to determine a threshold based on the at least one determined parameter represented by the recorded data and the estimated movement and/or posture. Since a movement and/or posture of the wearer may influence both the determination of the parameter(s) by the measurement circuit and also the risk of an incontinence event this embodiment enables a threshold to be determined based also on the estimated movement and/or posture the wearer had at the time of the incontinence event. Thresholds may thus be associated with movements and/or postures.

According to one embodiment the measurement circuit is arranged to repeatedly determine at least one parameter which varies with a fill level of the urine bladder and the processing circuit is further arranged to compare the repeatedly determined parameters to one or more urine bladder fill thresholds, each threshold being associated with an orientation or a movement determined by the sensor. The advantage of this embodiment may be understood from the previous embodiment.

According to one embodiment the processing circuit is further arranged to, subsequent to detecting a urination event (e.g. by detecting that the urine sensitive circuit has been exposed to urine), perform a comparison between: the at least one parameter represented by the data recorded in response to the detection of the urination event, and a parameter determined by the measurement circuit at an instant subsequent to the detection of the urination event. By comparing the fill level of the level prior to and after urination urinary retention problems may be identified.

According to one embodiment, which is contemplated to also form a separate inventive aspect there is provided a system comprising:
  a skin proximity sensor arranged to present a first electrical characteristic or response when being proximate to the skin of a user and a second electrical characteristic or response when being remote from the skin of the user;
  a measurement circuit arranged to perform a measurement on a urine bladder of a wearer to determine a parameter which varies with a fill level of the urine bladder; and
  a processing circuit arranged to:
    in response to detecting a separation between the skin proximity sensor and the skin of the user based on a changed electrical characteristic or response of the skin proximity sensor, record data representing a first parameter determined by the measurement circuit and indicating a urine bladder fill level at a first instant at or prior to the detection of the separation, and
    record data representing a second parameter determined by the measurement circuit and indicating a urine bladder fill level at a second instant which is later than the first instant.

The processing circuit may be arranged to perform a comparison between the first and the second parameter.

The second time instant may be delayed with respect to the first time instant by a predetermined time interval (e.g. an assumed duration of a normal urination). Alternatively the second time instant may correspond to an instant subsequent to or at which the processing circuit detects a restored proximity of the skin proximity sensor to the skin.

The skin proximity sensor may be arranged to be attached to e.g. an absorbent article worn by the user (such as a diaper/nappy or underwear/undergarment) or an upper edge of for example clothing (such as a pair trousers, a pair of shorts, a skirt or the like worn by the user). When the user pulls down the absorbent article or the clothing to urinate in the toilet the skin proximity sensor may lose the proximity with the skin. When the user pulls up the absorbent article or the clothing after the urination the skin proximity sensor may regain proximity with the skin. By comparing the fill level of the level prior to and after urination urinary retention problems may be identified.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings, where like reference numerals will be used for like elements, wherein.

DETAILED DESCRIPTION OF PREFERRED EMBODIMENTS

Detailed embodiments of aspects of the present inventive concept will now be described with reference to the drawings.

Figure 1:
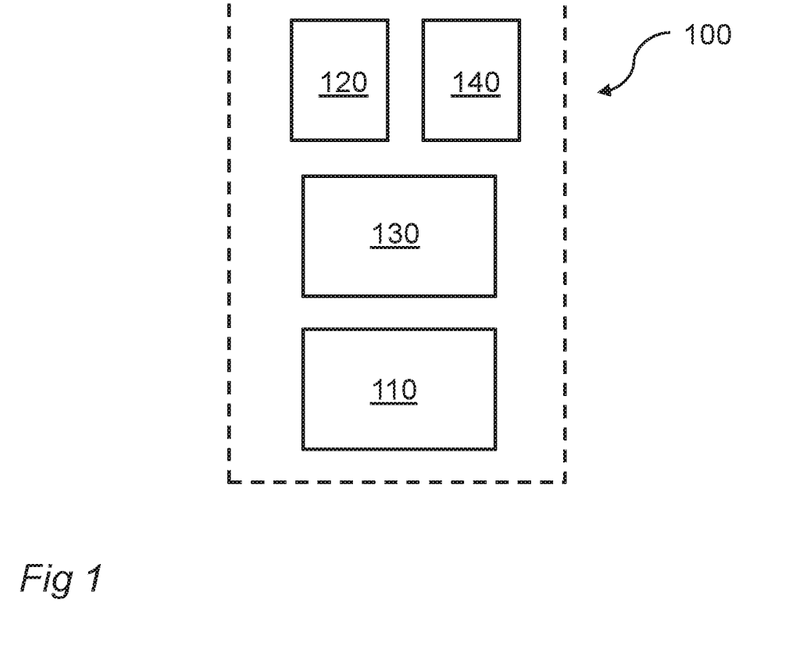
FIG. 1 is a schematic illustration of a system in accordance with an embodiment.

FIG. 1 schematically illustrates an embodiment of a system 100 for monitoring incontinence. The system 100 comprises a urine sensitive circuit 110, a measurement circuit 120 and a processing circuit 130. The urine sensitive circuit 110 is arranged to present a changed electrical characteristic when exposed to urine. In other words the urine sensitive circuit 110 may, in response to being exposed to urine, present a changed electrical characteristic or electrical property. As will described in further detail below, the changed electrical characteristic of the urine sensitive circuit 110 may be indicative of or proportional to the amount of urine released on to the urine sensitive circuit 110. In use, the urine sensitive circuit 110 may typically be positioned in a crotch region of the wearer, for example at an absorbent article (e.g. a diaper/nappy, a sanitary napkin/pad, or some other article for absorbing urine) or in connection to the underwear or undergarment. The wearer may also be referred to as a user of the system 100. If an incontinence event occurs urine may be released onto the absorbent article or the underwear of the wearer wherein the urine sensitive circuit 110 may be exposed to the urine.

The processing circuit 130 is arranged to determine whether the urine sensitive circuit 110 has been exposed to urine. As will be described in further detail below, the processing circuit 130 may be arranged to communicate (e.g. over a wireless or wired interface) with the urine sensitive circuit 110 and determine that the urine sensitive circuit 110 has been exposed to urine by detecting that an electrical characteristic of the urine sensitive circuit 110 has changed. The processing circuit 130 may also give a signal to the user (e.g. over a wireless or wired interface) that the absorbent article (e.g. a diaper/nappy, a sanitary napkin/pad, or some other article for absorbing urine) may be saturated and has to be changed. This will avoid leakage of the absorbent article. Meanwhile, the measurement circuit 120 is arranged to perform a measurement on a urine bladder of the wearer to determine at least one parameter which varies with a fill level of the urine bladder. The parameter(s) determined by the measurement circuit 120 may for example be an impedance of the urine bladder and/or an ultrasound measurement of the bladder size. Further examples will be given below. The measurement circuit 120 may typically be positioned at or near the bladder region of the wearer. The measurement circuit 120 may for example be provided in a unit which is secured to the skin at the bladder region (e.g. by means of an adhesive), secured to the wearer by means of a strap or secured to an edge of the diaper or underwear.

The system 100 further includes a sensor 140 which is arranged to be attached on the wearer, and determine an orientation and/or a movement of the sensor 140. The sensor 140 may include an accelerometer and/or a gyroscope, for example in the form of MEMS devices. The accelerometer may be a single-axis accelerometer, a dual axis accelerometer or a three-axis accelerometer. The accelerometer may provide measurements of the orientation and/or movement, e.g. by storing the measurements in a memory or buffer accessible by the processing circuit 130. The sensor 140 may be arranged to store a predetermined number of measurements and start discarding the oldest measurement when the predetermined number is exceeded. This may for example be conveniently implemented using a first-in-first-out buffer (i.e. a FIFO-buffer). The processing circuit 130 may based on the orientation and/or movement measurements, estimate a movement and/or posture of the wearer of the sensor 140. By comparing movement measurements during a time interval, the processing circuit 130 may determine whether the wearer was moving during the time interval and/or estimate a posture of the wearer. The processing circuit 130 may optionally also characterize the type of movement as movement by walking, by running, or by the wearer changing orientation or posture. As a non-limiting example, if an axis of an accelerometer is oriented along the length direction of the body, the accelerometer may provide a signal corresponding to the acceleration due to gravity when the user is standing up, and a signal close to zero when the user is lying down. This concept may be expanded to be able to identify further postures.

The movement pattern and posture of the wearer of the sensor 140 may further affect whether a present urine bladder fill level implies an increased risk for an involuntary urination event. It may also affect the parameter measurement(s), in particular an impedance measured by the measurement circuit 120.

Accordingly, the processing circuit 130 is further arranged to, in response to determining that the urine sensitive circuit 110 has been exposed to urine, estimate an amount of urine released on to the urine sensitive circuit 110 and record data representing the at least one parameter determined by the measurement circuit 120, an estimated movement and/or posture of the wearer based on an orientation or a movement determined by the sensor 140, and an estimate of the amount of urine released on to the urine sensitive circuit 110. The combination of data representing the parameter measurement(s), the estimated amount of urine and the movement/posture may enable a more accurate and extensive analysis of the incontinence events of the wearer since the occurrence of an incontinence event may be correlated to both a movement pattern or posture (i.e. an activity) of the wearer and the urine bladder fill level.

The processing circuit 130 may be arranged in a same unit as the measurement circuit 120 and galvanically connected to the measurement circuit 120. The sensor 140 may be provided in a same unit as the measurement circuit and/or the processing circuit 130. The measurement circuit 120, the processing circuit 130 and the sensor 140 may also be arranged on separate carriers (e.g. different circuit boards or different substrates) wherein the measurement circuit 120 and the sensor 140 may be connected to the processing circuit 130 by wires or a respective plug-socket interface. The measurement circuit 120, the processing circuit 130 and the sensor 140 may also be arranged on a same carrier wherein the circuits 120, 130 and the sensor 140 may be connected by a set of conductive paths.

The electrical characteristic of the urine sensitive circuit 110 may change from a first characteristic to a second characteristic when the urine exposure is increased (i.e. due to an incontinence event). It should be understood that a changed electrical characteristic may occur as a result of the urine sensitive circuit 110 changing from a relatively dry condition (e.g. before occurrence of an incontinence event) to a relatively moist condition (e.g. upon occurrence of an incontinence event). The changed characteristic may also occur as a result of the urine sensitive circuit 110 changing from an already moist condition (e.g. as a result of a first incontinence event) to an even more moist condition (e.g. as a result of a second incontinence event, subsequent to the first incontinence event). Thus the electrical characteristic may change in a manner which is proportional to the amount of urine to which the urine sensitive circuit 110 is exposed. In other words, the changed electrical characteristic of the urine sensitive circuit 110 may be indicative or proportional to the amount of urine released on to the urine sensitive circuit 110.

Moreover, an exposure to urine for the urine sensitive circuit 110 may in this context not necessarily imply a direct contact with the urine. In fact, the urine sensitive circuit 110 may be embedded in the absorbent material and thus not come into direct contact to urine released by the wearer. However, the presence of urine proximate to the urine sensitive circuit may nevertheless cause a changed electrical characteristic.

According to some embodiments the urine sensitive circuit 110 may be arranged to present an electrical response when exposed to urine, and wherein the processing circuit 130 is arranged to determine that the urine sensitive circuit 110 has been exposed to urine by detecting the electrical response of the urine sensitive circuit 110. The electrical response of the urine sensitive circuit 110 may further be indicative of or proportional to the amount of urine released on to the urine sensitive circuit 110, and wherein the processing circuit 130 is arranged to estimate the amount of urine released on to the urine sensitive circuit 110 based on the electrical response of the urine sensitive circuit 110.

The changed electrical characteristic or the electrical response of the urine sensitive circuit 110 may for example include a changed electrical parameter of the urine sensitive circuit 110. The particular type of electrical parameter which is changed may depend on the actual design of the urine sensitive circuit 110 (e.g. which circuit elements are included in the circuit 110) and may for example include one or a combination of a changed resistance, a changed inductance, a changed capacitance or a changed impedance. As will be described in more detail below, the changed electrical characteristic or the electrical response may also include a changed energy absorption of an incoming radiofrequency signal, and/or a changed energy of a radiofrequency signal transmitted from the urine sensitive circuit 110 (e.g. due to a changed resonance frequency of the urine sensitive circuit 110 and/or signal attenuation due to absorption of the transmitted/received radiofrequency signal by urine at the urine sensitive circuit 110). As will also be described in more detail below, the changed electrical characteristic may also include a changed voltage at a pair of electrodes (e.g. an anode-cathode pair) of the urine sensitive circuit 110.

As also will be described below the processing circuit 130 may be arranged to estimate the amount of urine released on to the urine sensitive circuit by determining a size of the change.

Figure 2:
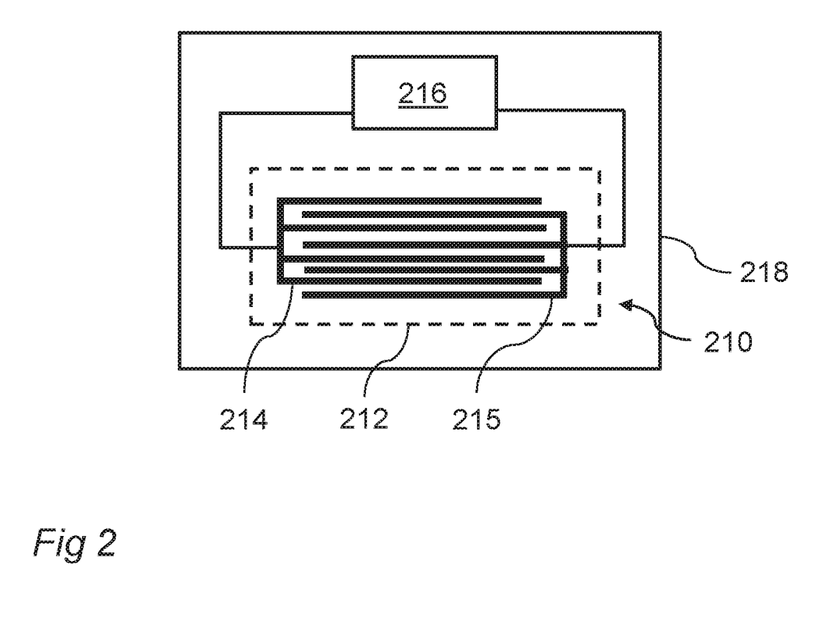
FIG. 2 illustrates an embodiment of a urine sensitive circuit.

FIG. 2 illustrates one embodiment of a urine sensitive circuit 210 which may be used as the urine sensitive circuit 110 in the system 100. The urine sensitive circuit 210 includes a portion 212 arranged to generate a current when exposed to urine. The urine sensitive circuit 210 includes a first and a second electrode 214, 215. The first electrode 214 is arranged to act as an anode and the second electrode 215 is arranged to act as a cathode when urine is present between the electrodes 214, 215. Thus, the urine may act as an electrolyte wherein a voltage may be generated between the first and the second electrode 214, 215. The urine sensitive circuit 210 is thus arranged to present a changed voltage characteristic and current characteristic when exposed to urine. The magnitude of the generated current may be proportional to a surface area of the portion 212 being exposed to urine. Various material combinations for the electrodes 214, 215 are possible. For example, the first electrode 214 may include copper and the second electrode 215 may include magnesium; the first electrode 214 may include copper and the second electrode 215 may include zinc; the first electrode 214 may include carbon and the second electrode 215 may include magnesium.

In the illustrated embodiment each one of the first electrode 214 and the second electrode 215 includes four elongate or finger-like electrode portions arranged in a comb-like structure. The electrode portions of the first and the second electrodes 214, 215 may, as illustrated, be arranged in an alternating fashion. Such an arrangement of the electrodes 214, 215 may be referred to as an interdigitated electrode structure. It should be noted that the number of electrode portions of the first and the second electrodes 214, 215 may be varied to generate a current falling within a desired range for a particular application and thus adapt the sensitivity of the urine sensitive circuit 210 in accordance with application requirements. As may be understood, a maximum current generated at the portion 212 will be limited by inter alia by the dimensions (e.g. length) of the electrodes, the amount of overlap between adjacent anode-cathode electrode portions and also the electrolyte concentration (ion concentration) in the urine. A generated current may hence be increased by providing a salt (e.g. sodium chloride) at the portion 212. The maximum current may also be proportional to the number of electrode portions of each electrode 214, 215. Although a greater number of electrode portions may result in a greater generated current, it is contemplated that in some applications a single electrode portion (e.g. a single "finger") of each electrode 214, 215 may suffice. It should also be noted that a greater number of electrode portions may provide a larger urine sensitive area of the urine sensitive circuit 210.

Optionally, a polymer coating, such as polyvinyl chloride (PVC) or polyurethane, may be applied at the portion 212 and/or to the electrodes 214, 215. More generally, the polymer may be a polymer which reacts with one or more specific analytes which may be present in the urine (e.g. creatinine, calcium or uric acid). The current generated at the portion 212 when exposed to urine (and the analytes present in the urine) may thereby be increased.

The first and the second electrode 214, 215 may be galvanically connected to a transmitter 216 of the urine sensitive circuit 210. A current generated at the electrodes 214, 215 may thus power the transmitter 216 to transmit a wireless signal from the urine sensitive circuit 210. As will be described further below, the wireless signal may be received by a receiver connected to the processing circuit 130 wherein the processing circuit 130 may determine that the urine sensitive circuit 210 has been exposed to urine.

A greater current generated at the portion 212 implies a greater power supplied to the transmitter 216. Thus a power of the wireless signal transmitted from the transmitter 216 may be indicative or proportional to the amount of urine released on to the portion 212. The processing circuit 130 may thus estimate the amount of urine released on to the urine sensitive circuit 210 by determining the strength of the received wireless signal (e.g. an absolute strength or a relative strength in relation to a predetermined reference value). The processing circuit 130 may for example measure a power of the received signal and compare the measured power with a look-up-table (LUT) associating predetermined (e.g. established by a calibration procedure) power levels with different amounts of urine exposure.

The transmitter 216 may generally include an LC-circuit or an RLC-circuit. Optionally, an antenna element may be connected to the LC- or RLC-circuit to improve the range of the transmitter 216. Alternatively, the electrodes 214, 215 may be designed to function as antenna elements. According to a specific example the transmitter 216 may be of the near-field communication-type (NFC) or a radio-frequency identification-type (RFID).

As illustrated in FIG. 2, the urine sensitive circuit 210 may be provided on a substrate 218. The substrate may generally be a relatively thin and flexible substrate. The circuit elements forming the urine sensitive circuit 210 may be formed by conducting portions provided on the substrate 218, e.g. by deposition of a conducting material on the substrate or by masking and etching of conducting material from the substrate, according to processes which per se are well-known to the skilled person. The substrate 218 may for example be a thin plastic foil, such as a PET-foil (Polyethylene terephthalate). One face of the substrate 218 may be provided with an adhesive. The urine sensitive circuit 210 may thus be arranged on a patch-like structure. An adhesive face may allow for easy attachment of the urine sensitive circuit 210 on an absorbent article or underwear and easy removal therefrom. Advantageously, the substrate 218 is biocompatible and environmentally friendly and is provided with a shape and a size minimizing inconvenience for the wearer throughout his/her daily activities. The substrate 218 may also include or be made of an absorbent material, such as paper, a cloth, cotton or absorbent polymers. The substrate itself may thus absorb the urine, wherein the absorbed urine in turn may cause a change of the electrical characteristic of the urine sensitive circuit 210. The substrate 218 with the urine sensitive circuit 210 may be arranged on an inside of the absorbent article (e.g. the diaper or the underwear) with the urine sensitive circuit 210 facing towards the absorbent article (wherein the substrate will be interposed between the urine sensitive circuit 210 and the skin) or towards the skin of the wearer. The urine sensitive circuit 210 may alternatively be arranged on an outside of the absorbent article wherein the urine sensitive circuit 210 may be exposed to urine absorbed by the absorbent article. According to a further option, the urine sensitive circuit 210 may alternatively be integrated in the absorbent article, for example within the absorbent material of a diaper or a sanitary napkin.

Figure 3:
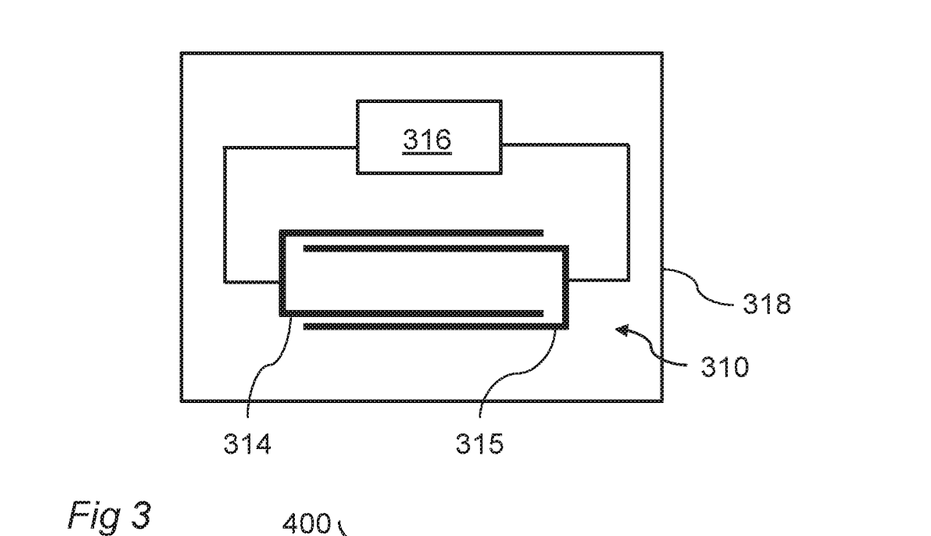
FIG. 3 illustrates another embodiment of a urine sensitive circuit.

FIG. 3 illustrates another embodiment of a urine sensitive circuit 310 which may be used as the urine sensitive circuit 110 in the system 100. The urine sensitive circuit 310 includes a first and a second electrode 314, 315. In contrast to the urine sensitive circuit 210, the first and the second electrode 314, 315 may be made of a same conducting material, for example copper. The first and the second electrode 314, 315 are arranged in an antenna configuration. The first and the second electrodes 314, 315 are connected to an LC- or RLC-circuit 316 wherein the urine sensitive circuit 310 may resonate in response to an incoming radiofrequency signal. When urine is present at the first and the second electrodes 314, 315 the resonance frequency of the urine sensitive circuit 310 may change (due to a change of the resistance or capacitance in the urine sensitive circuit 310 such as between the first and the second electrode 314, 315). As will be described in more detail below, the radiofrequency signal may be transmitted by a transmitter connected to the processing circuit 130. The processing circuit 130 may thus determine that the urine sensitive circuit 310 has been exposed to urine based on a changed response to the transmitted radio frequency signal.

The change of the resonance frequency of the urine sensitive circuit 310 may be affected by the amount of urine released on to the urine sensitive circuit 310. In other words, the presence of urine changes the environment around the first and the second electrodes 314, 315 whereby a resonance condition for the urine sensitive circuit 310 is changed. The larger change of the environment the larger is the change of the resonance condition. The change in the environment may for example induce a shift, a broadening and/or a spectral change of the resonance condition such that the amount of urine may be determined from the affected resonance condition. The processing circuit 130 may thereby estimate the amount of urine released on the urine sensitive circuit 310. The processing circuit 130 may for example measure a power of the received response, or a duration of the received response and compare the measured power with a look-up-table (LUT) associating predetermined (e.g. established by a calibration procedure) powers or durations with different amounts of urine exposure.

With reference to FIG. 3, the number of "finger-like" electrode portions of each electrode 314, 315 may be greater or smaller than two. As noted above, a greater number of electrode portions may provide a larger urine sensitive area of the urine sensitive circuit 310. Moreover, the design and dimensions of the electrodes 314, 315 may be varied to obtain, on the one hand a sufficient coupling to an incoming RF field and, on the other hand, a desired sensitivity to urine for the particular application.

According to an alternative embodiment, which also will be described in relation to FIG. 2, a current generated at the portion 212 may, instead of powering transmission of a wireless signal, be used for powering an increment of a counter stored in a memory of the urine sensitive circuit 210. For the purpose of the following discussion, element 216 in FIG. 2 may represent both the memory and transmitter-receiver circuitry. The processing circuit may further be arranged to estimate the amount of urine released on to the urine sensitive circuit based on the counter.

The memory of the urine sensitive circuit 210 may for example include an N-bit register and be arranged to shift a number of bits in the register from "0" to "1" when a current/voltage exceeds a current/voltage level) required to power the memory (which as understood by the skilled person may be specific for the particular type and implementation of the memory). The number of shifted bits may be proportional to the voltage/current provided from the portion 212. As a non-limiting example, release of 1 ml of urine on to the portion 212 may result in shifting of one bit in the register from "0" to "1". Release of an additional 1 ml of urine on to the portion 212 may result in a doubling of the current/voltage generated at the portion 212 and thus result in shifting of one more bit in the register from "0" to "1". Preferably, the memory is a non-volatile memory wherein the state of the bit register will maintained even when the memory is not powered. Thereby, the state of the bit register (and thus value of the counter) may be saved even if the portion 212 becomes before a subsequent release of urine or a read-out of the memory has been performed.

The transmitter-receiver circuitry of the urine sensitive circuit 210 may be arranged to, in response to receiving a wireless read-out signal from a read-out unit (for example the processing circuit 130 transmitting the wireless signal using a transmitter connected to the processing circuit 130), encode the value of the counter into a response signal and transmit the response signal wirelessly to the read-out unit using techniques which are well-known to the skilled person. Optionally, the counter in the memory of the urine sensitive circuit 210 may be reset to zero following read-out. The read-out signal is preferably transmitted at a fixed repetition rate (such as every 5-30 seconds, every 1-5 minutes). The operation of the transmitter-receiver circuitry and the memory during read-out may, using well-known circuit designs, be powered by the energy of the received wireless signal from the read-out unit. The operation may however also be powered by a small battery.

The logic governing the updating, read-out and initialization of the memory as well as the operation of the transmitter-receiver may for example be implemented in an integrated circuit which is connected to the electrodes 214, 215. To avoid or reduce possibly undesired shifting of the resonance frequency of the urine sensitive circuit 210, a fluid impermeable layer or encapsulation (e.g. plastic) may be arranged to cover the urine sensitive circuit 210 but exposing the portion 212 with the electrodes 214, 215. Thereby, urine exposure of other parts than the portion 212 of the urine sensitive circuit 210 may be avoided or minimized. Similar to avoid electrical artifacts from the environment on the urine sensitive circuit 210, an isolation layer, e.g. from a metal material (the same or different material as used for the electrodes of the urine sensitive circuit 210), may be arranged on an underside of the substrate 218, opposite to the face provided with the circuit 210.

The urine sensitive circuit 210 may further include a timer wherein a value of the timer at each counter increment may be recorded in the memory, along with the value of the counter. The recorded timer values may also be encoded into the response signal transmitted to the read-out unit. Thereby, the read-out unit may determine a relative timing of the counter increments. The timer may be powered by a same battery as the transmitter-receiver circuitry and the memory. The timer may also be powered by a energy storage element such as a capacitor which is charged by the current generated at the portion 212. Preferably, the energy stored in the energy storage element is sufficient for powering the timer for a duration which equals or exceeds the repetition rate of the wireless read-out signal from the read-out unit. Optionally, the timer (in addition to the counter in the memory of the urine sensitive circuit 210) may be reset to zero following each read-out.

With reference to FIG. 1, the measurement circuit 120 is arranged to perform a measurement on the urine bladder to determine a parameter which varies with a fill level of the urine bladder. According to one embodiment, the measurement circuit 120 may be arranged to measure an impedance of the urine bladder of the wearer of the measurement circuit 120. Typically, as the amount of urine in the urine bladder increases (i.e. the urine bladder fill level increases) an impedance measured across the urine bladder will increase. The determined impedance hence forms a measurable parameter which varies with the urine bladder fill level. The measurement circuit 120 (which in this case may be referred to as an impedance measurement circuit 120) may be arranged to transmit an electrical measurement signal through the urine bladder of the wearer. The measurement signal may be an alternating current signal. As a non-limiting example, the frequency may for example be in the range 5 kHz to 200 kHz. As a non-limiting example, the current may be in the range 10 µA to 1000 µA.

The processing circuit 130 may for example compare the measured impedance with a look-up-table (LUT) associating predetermined (e.g. established by a calibration procedure) impedance values with different urine bladder fill levels.

The measurement circuit 120 may be arranged to perform a two-terminal measurement of the impedance. The measurement circuit 120 may be arranged to transmit the measurement signal from a first skin electrode, arranged to be attached to the skin of the wearer at a first side of the urine bladder, through the urine bladder, to a second skin electrode, arranged to be attached to the skin of the wearer at a second side (advantageously generally opposite to the first side) of the urine bladder and determined the impedance of the urine bladder based on the transmitted measurement signal and the measurement signal as received by the second skin electrode. Alternatively, the measurement circuit 120 may be arranged to perform a four-terminal measurement of the impedance. Thereby a contribution of the electrode-skin contact resistance may be compensated for. In any case, the electrodes may be of a dry type or, to improve the contact between the electrodes and the skin, of a gel type or wet type.

The measurement circuit 120 may be arranged to repeatedly measure the impedance of the urine bladder. A measured impedance may be digitized by an analog-to-digital converter of the measurement circuit 120 and stored in a memory or buffer accessible by the processing circuit 130.

The measurement circuit 120 may be arranged to store a predetermined number of measured impedances and start discarding the oldest impedance measurement when the predetermined number is exceeded. This may for example be conveniently implemented using a first-in-first-out buffer (i.e. a FIFO-buffer).

As an alternative to the measurement circuit 120 digitizing the measured impedance, an analog signal representative of the measured impedance may be provided to the processing circuit 130 which may digitize the received analog signal using an analog-to-digital converter of the processing circuit 130 and store the digitized signal in a memory or buffer accessible by the processing circuit 130.

According to an alternative embodiment, the measurement circuit 120 may be arranged to perform an ultrasound measurement on the urine bladder. More specifically, the measurement circuit 120 may determine or estimate a dimension of the urine bladder. The dimension may for example be a width of the urine bladder. Typically, as the amount of urine in the urine bladder increases (i.e. the urine bladder fill level increases) the urine bladder will expand wherein a width dimension of the urine bladder will increase. The determined width may hence form a measurable parameter which varies with the urine bladder fill level. The measurement circuit 120 (which in this case may be referred to as an ultrasound measurement circuit 120) may be arranged include an ultrasonic transducer arranged transmit an ultrasonic signal and receive ultrasonic echo signals. The ultrasonic transducer may be arranged to, in use of the measurement circuit 120, face a skin portion at the bladder region of the wearer. As the urine bladder expands the time between the echo signal resulting from a reflection at the bladder wall closest to the transducer and the echo signal resulting from a reflection at the remote and opposite bladder wall will increase. Similarly to the case of measuring the impedance described above, the transducer may be arranged to store the time difference between these two echo signals in a memory or buffer accessible by the processing circuit 130, for example in a FIFO-buffer as described above). To improve the accuracy of the ultrasound measurement, the measurement circuit 120 could be provided with an array of ultrasonic transducers wherein a more accurate estimate of the bladder expansion could be obtained based on width dimensions of the bladder at a plurality of positions.

Although described as alternatives in the above, it would also be possible to design the measurement circuit 120 to perform an impedance measurement as well as an ultrasound measurement on the urine bladder. By determining and correlating both of these two different types of parameters the accuracy of the urine bladder fill level may be improved.

In addition to the above measurements relating to the urine bladder fill level, the measurement circuit 120 may be arranged to (as an alternative to the impedance and ultrasound measurement, or in addition thereto) perform one or a combination of a magnetic field measurement on the bladder, a light reflection measurement on the bladder or a mechanical measurement of the bladder size or bladder pressure.

For the magnetic measurement, the measurement circuit 120 may include an inductor circuit generating an oscillating magnetic field through the urine bladder. As the urine bladder fill level increases, the increased amount of urine in the bladder may induce eddy currents in the inductor circuit and consequently an increased energy may be dissipated by the magnetic field. A parameter proportional to this change may be determined and digitized by an analog-to-digital converter of the measurement circuit 120. In line with the above description of the measurement circuit 120, the determined parameter may be stored in a memory or buffer accessible by the processing circuit 130, for example in a FIFO-buffer as described above).

For the light reflection measurement, the measurement circuit 120 may include an optical transducer (for example a light emitting diode and a photo detector). As a non-limiting example the wavelength of the light may be in the infrared or near-infrared region. The optical transducer may be arranged to, in use of the measurement circuit 120, face a skin portion at the bladder region of the wearer. As the urine bladder expands the blood flow characteristic of the bladder will change. This will affect the reflected optical energy received by the photodiode. The reflected light detected by the photo detector may thus form a parameter representative of the bladder fill level. The power detected by the photo detector may be digitized by an analog-to-digital converter of the measurement circuit 120. In line with the above description of the measurement circuit 120, a value of the detected power may be stored in a memory or buffer accessible by the processing circuit 130, for example in a FIFO-buffer as described above).

For the mechanical measurement, the measurement circuit 120 may be arranged to measure a resistance of a strain gauge adhesively attached to the skin at the bladder region, or incorporated in a flexible belt arranged to be provided about the waist of the wearer. As the bladder expands, the electrical resistance of the strain gauge may increase. The resistance may thus form a parameter representative of the bladder fill level. The resistance of the strain gauge, measured by the measurement circuit 120 may be digitized by an analog-to-digital converter of the measurement circuit 120. In line with the above description of the measurement circuit 120, a value of the resistance may be stored in a memory or buffer accessible by the processing circuit 130, for example in a FIFO-buffer as described above). By the measurement circuit 120 optionally sampling and recording a signal of an accelerometer arranged on the skin of the wearer (in proximity to the strain gauge or more generally on the belly region of the wearer), the influence of strain of the strain gauge induced by breathing may be compensated for.

As described above, the processing circuit 130 is arranged to, in response to determining that the urine sensitive circuit 110 has been exposed to urine, estimate an amount of urine released on to the urine sensitive circuit 110 and record data representing the at least one parameter as determined by the measurement circuit 120, an estimated movement and/or posture of the wearer based on an orientation and/or a movement as determined by the sensor 140, and an estimate of the amount of urine released on to the urine sensitive circuit 110. In particular, the processing circuit 130 may be arranged to record data representative of the parameter(s) as determined by the measurement circuit 120 at an instant immediately preceding the detection of the urination event by the processing circuit 130 e.g. by retrieving a last stored parameter, as determined by the measurement circuit 120, from the above-mentioned memory or buffer accessible by the processing circuit 130. Additionally, the processing circuit 130 may, as discussed above, estimate a movement/posture of the wearer based on movement and/or orientation measurements by the sensor 140. Thereby, the recorded data may be used to correlate a urine bladder fill level with the occurrence of a urination or incontinence event, a movement and/or posture of the wearer as well as an amount of released urine. The data may be recorded in a memory of the processing circuit 130. This recorded data may be stored for transmission to an external unit, or for further analysis.

More specifically, the processing circuit 130 may record the data in a data structure linking the at least one parameter as determined by the measurement circuit 120, an estimated movement/posture and an estimate of the amount of urine released on to the urine sensitive circuit 110 to the detected urination event. The data may for example be stored in an array data structure or as entries in a database, associating the at least one parameter as determined by the measurement circuit 120, an estimated movement/posture and an estimate of the amount of urine released on to the urine sensitive circuit 110 with the detected urination event. Along with the data, an indication of that the urine sensitive circuit has been exposed to urine may be stored, for example using a single-bit binary flag. Optionally, the system 100 may include a timer wherein a time of the detection of the urination event may be recorded in the data structure. The stored time may for example correspond to a time of day.

The processing circuit 130 may also be arranged to continuously, or repeatedly compare the data representing the parameter(s) as determined by the measurement circuit 120 to a respective threshold. For example, if the measurement circuit 120 is arranged to determine the impedance of the urine bladder, the threshold may be an impedance threshold which corresponds to a urine bladder fill level at which the risk of an involuntary urination event is substantially increased. The impedance threshold may thus be referred to as a urine bladder fill threshold. The threshold may be stored in a memory accessible to the processing circuit 130. If the processing circuit 130 determines that the threshold is met or exceeded an alert signal (i.e. warning signal) may be provided to the wearer to indicate that the risk of an involuntary urination event is increased. Advantageously, the processing circuit 130 may provide the signal to the wearer already when a determined impedance differs from the threshold by less than a predetermined amount, adapted to give the wearer some time to e.g. go to the toilet (e.g. 10 minutes or 20 minutes in advance before the time when an incontinence event is expected to occur). The signal may be a visual, audible and/or tactile signal generated by a visual indicator (e.g. a display or a LED), an audible indicator (e.g. a speaker) connected to the processing circuit 130 or tactile indicator (e.g. a vibrator). Alternatively, the signal may be provided by the processing circuit 130 to an external device (e.g. a mobile phone, a tablet computer or a personal computer) which may present a warning on a display thereof or generating an audible warning.

The above described impedance-based threshold comparison may be made in a corresponding manner also for the other parameter types which the measurement circuit 120 may determine, as described above. Thus, each type of parameter threshold may be referred to as respective a urine bladder fill threshold. The processing circuit 130 may be arranged to provide a warning signal in response to any one of the determined parameter(s) meeting or exceeding its associated threshold.

The threshold(s) may be predetermined, for example during a calibration phase of the system 100. According to an alternative embodiment, the processing circuit 130 may be arranged to determine the threshold(s). The processing circuit 130 may set or configure each threshold based on the parameter(s) determined by the measurement circuit 120 and represented by the data recorded by the processing circuit 130 in response to detecting the incontinence event. The processing circuit may be arranged to set or configure each threshold for example in response to a first detected urination event. Optionally, the processing circuit may set or configure each threshold based on both the parameter(s) determined by the measurement circuit 120 and a previously determined threshold. For example, if the data recorded by the processing circuit 130 in response to detection of an urination event represents a parameter value which is smaller than a previous threshold, a new threshold may be configured to be smaller than the previous threshold. Conversely, if the data recorded by the processing circuit 130 in response to detection of an urination event represents a parameter value which is greater than a previous threshold, a new threshold may be configured to be greater than the previous threshold. Thereby the threshold(s) may be adapted based on the bladder fill level at the time of the actual occurrences of urination events.

Optionally, the processing circuit 130 may be arranged to repeatedly provide a signal which is indicative of a urine bladder fill level. The signal may for example indicate a value or values of the parameter(s) most recently determined by the measurement circuit 120. The signal may also be indicative of a ratio or ratios between a value or values of the parameter(s) most recently determined by the measurement circuit 120, and associated parameter thresholds. The signal may for example be provided to a display providing information allowing the urine bladder fill level to be determined parameter. The value(s) and/or ratio(s) may for example be presented on a display connected to the processing circuit 120. Alternatively, the signal may be provided by the processing circuit 120 to an external device (e.g. a mobile phone, a tablet computer or a personal computer) which may present the value(s) and/or ratio(s) on a display.

In case the processing circuit 130 is arranged to perform threshold comparisons, as described above, a parameter threshold may preferably be associated with a respective movement or posture of the wearer. For example, a first impedance threshold may be used when the wearer is lying down and a second impedance threshold may be used when the wearer is upright or is walking. As a non-limiting example, it may be predetermined by a clinician that a particular persons urine bladder may be half-full if it contains 350 mL of fluid and an impedance of 40 ohm when the person is lying down and an impedance of 42 ohm or 38 ohm when the person is seated upright. By determining the impedance of the urine bladder for a plurality of different postures or movement types, a plurality of thresholds may be determined, each associated with a particular posture or movement type. The thresholds may be stored in a memory or buffer accessible to the processing circuit 130.

Figure 4:
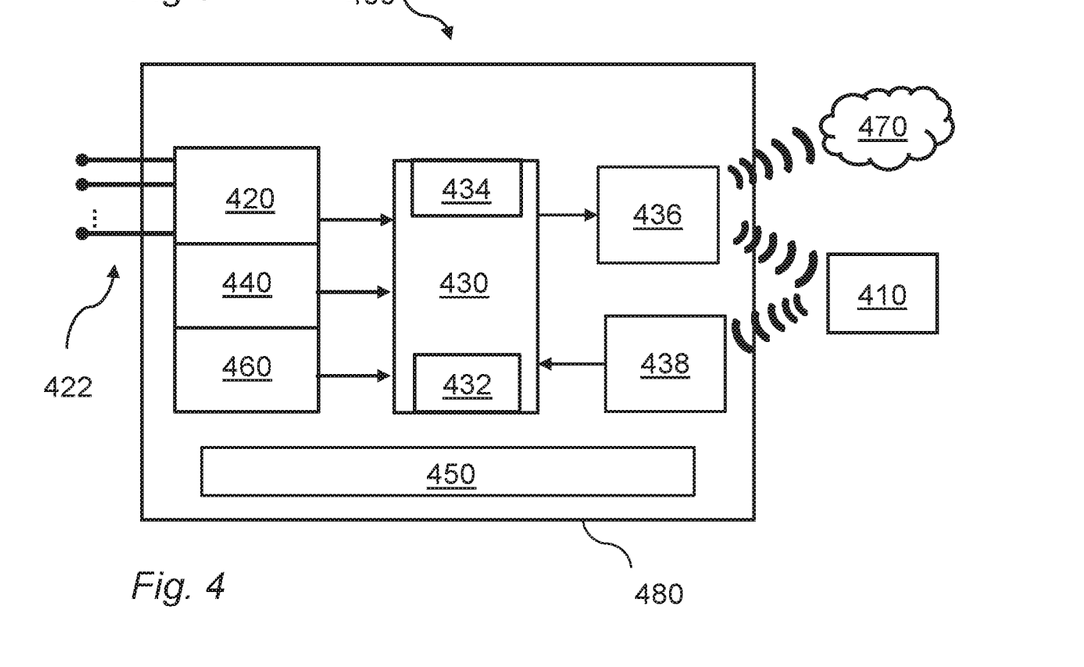
FIG. 4 is a schematic illustration of a system in accordance with a further embodiment.

FIG. 4 illustrates a further embodiment of a system 400 for monitoring incontinence. The system 400 includes a urine sensitive circuit 410. The urine sensitive circuit 410 may be implemented in accordance with the urine sensitive circuit 210 or 310 described above. The system 400 further includes a measurement circuit 420, corresponding to the measurement circuit 120, and a sensor 440 corresponding to the sensor 140. The measurement circuit 420 may for example measure an impedance of the urine bladder using the skin electrodes 422. The system 400 further includes a processing circuit 430, corresponding to the processing circuit 130. The processing circuit 430 includes a memory 434 for recording data representing parameter(s) related to the urine bladder fill level determined by the measurement circuit 420, data representing the movement and/or posture of the wearer, as well as thresholds and data representing estimated amounts of urine released. The processing circuit 430 may further include an analog-to-digital converter 432 for digitizing for example measurement signals from the measurement circuit 420, the sensor 440 and additional sensors 460. The system 400 may further include a battery 430 for powering the measurement circuit 420, the processing circuit 430, the transmitter 436, the receiver 438, and the sensor 440 as well as optional additional sensors described below. The transmitter 436 may include both transmitter portion for supporting communication with an external device or a communication network (for example a Bluetooth® protocol such as Bluetooth® low energy) as well as a transmitter portion for sending read-out or interrogation signals to the urine sensitive circuit (e.g. using NFC). Likewise, the receiver 438 may include both a receiver portion for supporting communication with the external device or the communication network (for example a Bluetooth® protocol such as Bluetooth® low energy) as well as a receiver portion for receiving signals from the urine sensitive circuit (e.g. using NFC).

Optionally, the system 400 may further include a user interface (not shown in FIG. 4) The user interface may include a user input device, such as a button or keypad, lights, speaker, and display, such as a liquid crystal (LCD) display or an light-emitting diode (LED) display. The speaker and/or the display may be used for providing indications and alerts to the user, as described above. The user interface may also include a tactile indicator, such as a vibrator, which may be used instead, or as a complement to the speaker and the display.

As schematically indicated in FIG. 4, the elements 420-460 may be arranged on a same carrier. The carrier may preferably be a relatively light-weight and unobtrusive unit which may be secured to the skin at the bladder region (e.g. by means of an adhesive) of the wearer, secured to the wearer by means of a strap or secured to an edge of the diaper or underwear.

The processing circuit 430 may include for example a micro processor or a CPU. The logic governing the operations of the processing circuit 430 may for example be stored as software instructions in a storage medium (typically non-transitory form), for example the memory 434, which instructions are arranged to perform the operations of the processing circuit 430 described herein when executed by the processing circuit 430. The memory 434 may be a volatile memory, e.g. a Random Access Memory (RAM) or a flash memory etc. The memory 434 may for example include a program section and a data section, wherein the program section may store the above-mentioned software instructions and the data section may store data and variables used to carry out the described operations. Alternatively, the functions of the processing circuit 430 may be implemented in one or more integrated circuits, or even in one or more application-specific integrated circuits (ASICs) or field-programmable gate arrays (FPGAs).

As indicated in FIG. 4, if the urine sensitive circuit 410 is implemented in accordance with the urine sensitive circuit 210, the urine sensitive circuit 410 may in response to being exposed to urine generate a current powering transmission of a wireless signal which may be received by the receiver 438 connected to the processing unit 430. The processing circuit 430 may, in response to detecting the wireless signal, determine that a urination event has occurred and accordingly record data representative of the parameter(s) (as determined by the measurement circuit 420 at an instant immediately preceding, or at a same time as, the detection of the wireless signal), an estimate of the amount of urine released on to the urine sensitive circuit, and an estimated movement and/or posture of the wearer. Alternatively, if the urine sensitive circuit 410 is implemented in accordance with the urine sensitive circuit 310, the processing circuit 430 may determine that a urination event has occurred when the response from the urine sensitive circuit 410 to a wireless signal transmitted by the transmitter 436 is changed. The processing circuit 430 may control the transmitter 436 to repeatedly transmit a wireless signal to the urine sensitive circuit 410 at a predetermined repetition-rate.

Optionally, the system 400 may include additional sensors, generally indicated as element 460 in FIG. 4. For example the system 400 may include a microphone for monitoring the urine flow during a controlled urination (typically referred to as voiding). The system 400 may further include a skin proximity sensor (e.g. a touch capacitive-based or resistive-based sensor which per se are well-known in the art for detecting skin proximity or contact). The skin proximity sensor may be arranged to provide a signal to the processing unit 430 in response to detecting reduced proximity or loss of contact with the skin of the wearer. The signal may indicate to the processing circuit 430 the detection of a "pants down" event. The event may be recorded in the memory 434 by the processing circuit 430 and associated with a current measurement of the measurement circuit 420 relating to the urine bladder fillness level. Since a "pants down" event may mean that the wearer has visited the toilet for an intentional urination (also known as voiding). It may for analysis and diagnosis purposes be valuable to record the fill level of the bladder at the time of the toilet visit. Optionally, the "pants down" event may trigger activation of the microphone, wherein the processing circuit 430, based on audio signals from the microphone, may analyze the sound of the urination to determine whether the flow of urine is continuous or intermittent, for example by analyzing the amplitude of the audio signal from the microphone. The processing circuit 430 may record this information (e.g. as a bit flag indicating either a continuous or an intermittent flow) together with the above-mentioned "pants down" event. Additionally, the processing circuit 430 may, record a measurement of the measurement circuit 420 relating to the urine bladder fill level after the voiding is finished. If the amount of urine remaining in the urine bladder exceeds a certain predetermined (and user specific) amount, e.g. 100 mL or 150 mL a warning signal may be generated (e.g. via the user interface of the system). Such a measurement of the urine bladder fill level after a urination may also be performed in response to the processing circuit detecting an incontinence event (i.e. by determining that the urine sensitive circuit 410 has been exposed to urine). Thus the system 400 may be used for urine retention detection. Urine retention detection may lead to urinary infections. It is contemplated that the processing circuit 430 may record also this information in the memory 434. Optionally, instead of a dedicated skin proximity sensor the urine sensitive circuit 410, which may present a changed electrical characteristic when proximate or in contact with the skin, may be used to detect the pants-down event.

Also, a temperature sensor for measuring a skin temperature and/or an ambient temperature may be provided in the system 400. The system 400 may also include an altimeter for measuring the altitude. Data related to the measurements performed by these additional sensors 460 may also be recorded by processing circuit 430 in the memory 434 in response to detecting an incontinence event. This additional data may enable an even more accurate and extensive analysis of the incontinence events of the wearer since the occurrence of an incontinence event may be correlated to additional parameters which may have an influence on the occurrence of the involuntary urination event.

The recorded data may repeatedly, or upon request, be transmitted by the transmitter 436 to an external device or a communication network generally indicated by element 470 in FIG. 4. The transmitter 436 may for example use the Bluetooth® low energy protocol. The external device 470 can for example be a mobile device of the wearer, a mobile device of a medical staff, and or a networked server. The external device may be a small, battery-powered, portable device such as a device intended to be placed next to the bed or in the room of the wearer or which accompanies the wearer of the system 400 throughout a daily routine. The external device may have a simple user interface, such as a button or keypad, and a display or other visual indicator. As a further example the external device may be a mobile phone. The transmitted data can in turn be used to provide indications on the mobile device to the wearer or the medical staff of an impending, or an already occurred incontinence event, an estimated bladder fill level and/or an amount of urine released. The transmitted data can also be used to perform analytical studies to determine an incontinence diagnose and suggest a treatment best suited for the user's condition.

For analysis and diagnosis purposes, the data recorded by the processing circuit 130, 430 may be used to establish a micturition log or micturition diary. For example, the diary may include the diurnal (day time) and nocturnal (night time) urine loss quantity and the time thereof, urine quantity in the bladder prior to voiding (normal urination) and the voiding time, the urine flow, movement and/or posture at the incontinence event and a present urine bladder fill level preceding each incontinence event.

As discussed earlier the system 100, 400 may be particularly useful for monitoring stress incontinence which. But it may also be useful for monitoring urge and mixed-type incontinence. Although it should be noted that some urge incontinence events may result in peak clipping of the urine amount estimations if the urine leakage exceeds the sensitivity range of the urine sensitive sensor 110, 210, 310, 410.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For example, instead of being wirelessly connected (and thus galvanically disconnected) the urine sensitive circuit 110 may be galvanically connected by wire to the processing circuit 130. The wires may for example be integrated in the undergarment or in the absorbent article. For example a urine sensitive circuit similar to the urine sensitive circuit 210 however without the transmitter 216 could be used wherein a current or voltage generated at the electrodes 214, 215 could be directly detected and measured by the processing circuit 130 using techniques which are well-known in the art. According to another example a urine sensitive circuit similar to the urine sensitive circuit 310 could be used wherein a changed impedance, resistance or capacitance between the electrodes 314, 315 could be directly detected and measured by the processing circuit 130. Accordingly, the processing circuit 130 may for example measure the voltage or current generated at the portion 212, or the impedance, capacitance or resistance between the electrodes 314, 315 and compare the measurement with a look-up-table (LUT) associating predetermined (e.g. established by a calibration procedure) current/voltage/impedance/capacitance/resistance levels with different amounts of urine exposure.

In these examples, the electrodes 214, 215, 314, 315 of the urine sensitive circuit 1 can for example be formed as thin layers on the substrate 218, 318. The layers may for example be of a micrometer thickness, wherein the electrodes may be flexible and thus may minimize discomfort for the wearer. To further reduce the weight of the electrodes 2149, 215, 314, 315 they may be perforated.

As an alternative or in addition to the above described measurements relating to the urine bladder fill level, it has further been contemplated that data relating to other parameters could be recorded, Accordingly there is provided a system for monitoring incontinence for a user, comprising:

a urine sensitive circuit (e.g. corresponding to the circuit 110, 210, 310 or 410) arranged to present a changed electrical characteristic when exposed to urine, a processing circuit (e.g. corresponding to the processing circuit 130 or 430) arranged to:

determine whether the urine sensitive circuit has been exposed to urine, and in response to determining that the urine sensitive circuit has been exposed to urine, record data representing a measured or user-supplied parameter that influences a urine bladder fill level.

The user-supplied parameter may be a volume of a fluid intake by the user, a type of fluid, a glomerular filtration rate (GFR), or a time of a last toilet visit. This parameter may for example be entered by the user e.g. via the above-mentioned user interface, or via a user interface of an external device (e.g. 470) and transmitted to the processing circuit (e.g. 430). Based on knowledge of the fluid intake of the user and the glomerular filtration rate the urine bladder fill level may be accurately estimated by a calculation without requiring direct measurements on the urine bladder. A clinician may determine the GFR parameter and introduce this in the memory of the processing unit (or alternatively in the memory of the external device). One method of determining GFR from is to collect urine (usually for 24 hours) to determine the amount of creatinine that was removed from the blood over a given time interval. If one removes, say, 1440 mg in 24 hours, this is equivalent to removing 1 mg/min. If the blood concentration is 0.01 mg/mL (1 mg/dL), then one can say that 100 mL/min of blood is being "cleared" of creatinine, since, to get 1 mg of creatinine, 100 mL of blood containing 0.01 mg/mL would need to have been cleared. The creatinine measure can then be correlated with, for example, the user's age, gender and race, to determine the user's GFR.

The measured parameter may represent a time passed since a last toilet visit (e.g. by determining the time passed since a last "pants down" event determined using the above described skin sensor), a temperature (at the time of determining that that the user has urinated on the absorbent article) or a time of day.

If the system includes a sensor (e.g. sensor 140 or 440) arranged to determine an orientation and/or a movement of the sensor, the recorded data may also represent an estimated movement and/or posture of the wearer based on an orientation and/or a movement determined by the sensor. If the system includes a measurement circuit (e.g. measurement circuit 120 or 420) the recorded data may also represent the parameter(s) determined by the measurement circuit. If the processing circuit is arranged to also estimate an amount of urine released on to the urine sensitive circuit, in response to determining that the urine sensitive circuit has been exposed to urine, the recorded data may also represent the estimated amount of urine released on to the urine sensitive circuit.

If used in combination with the above-described embodiments including a measurement circuit arranged to perform a measurement on a urine bladder of a wearer to determine at least one parameter which varies with a fill level of the urine bladder, the recording of both parameter(s) having an influence on a urine bladder fill level and parameter(s) varying with a fill level of the urine bladder may thus enable an even more detailed and complete analysis and diagnosis of the incontinence.

The invention claimed is:

1. A system for monitoring incontinence for a user comprising:

a urine sensitive circuit configured to present a changed electrical characteristic when exposed to urine, wherein the changed electrical characteristic of the urine sensitive circuit is indicative of an amount of urine released on to the urine sensitive circuit;

a measurement circuit configured to perform a measurement on a urine bladder of the user to determine at least one parameter which varies with a fill level of the urine bladder;

a sensor configured to be attached on the user and determine an orientation and/or a movement of the sensor; and a processing circuit configured to:

determine whether the urine sensitive circuit has been exposed to urine, estimate the amount of urine released on to the urine sensitive circuit, and in response to determining that the urine sensitive circuit has been exposed to urine, record data representing said at least one parameter determined by the measurement circuit, an estimated movement and/or posture of the user based on an orientation and/or a movement determined by the sensor, and an estimate of the amount of urine released on to the urine sensitive circuit.

2. The system according to claim 1, wherein the changed electrical characteristic circuit includes one or more selected from the group comprising: a changed resistance, a changed capacitance, a changed inductance, a changed impedance, a changed resonance frequency, a changed voltage generated by the urine sensitive circuit, a changed current generated by the urine sensitive circuit, a changed resonance frequency of the urine sensitive circuit.

3. The system according to claim 2, wherein the processing circuit is configured to estimate the amount of urine released on to the urine sensitive circuit by determining a size of the change.

4. The system according to claim 1, wherein the processing circuit is configured to provide a signal which is indicative of a urine bladder fill level based on the at least one determined parameter.

5. The system according to claim 1, wherein the measurement circuit is configured to be positioned at or near a bladder region of the user and wherein the sensor is configured in a same unit as the measurement circuit.

6. The system according to claim 1, further comprising an underwear or undergarment wherein the urine sensitive circuit is configured to be positioned in connection to the underwear or undergarment.

7. The system according to claim 6, wherein the measurement circuit is configured to be secured to an edge of the underwear or undergarment.

8. The system according to claim 1, wherein the processing circuit is further configured to, subsequent to detecting that the urine sensitive circuit has been exposed to urine, perform a comparison between: the at least one parameter represented by the data recorded in response to said detecting, and a parameter determined by the measurement circuit at an instant subsequent to the detection of the urination event.

9. The system according to claim 1, wherein the measurement circuit is configured to repeatedly determine at least one parameter which varies with a fill level of the urine bladder and the processing circuit is further configured to compare the repeatedly determined parameters to one or more urine bladder fill thresholds, each threshold being associated with a movement or a posture, wherein the processing circuit is further configured to provide a warning signal in response to said at least one parameter which varies with a fill level of the urine bladder meeting or exceeding its associated threshold.

10. The system according to claim 1, wherein the processing circuit is further configured to, in response to detecting a urination event by detecting that the urine sensitive circuit has been exposed to urine, record an association between said at least one parameter determined by the measurement circuit, the estimated movement and/or posture and the estimate of the amount of urine released on to the urine sensitive circuit.

11. The system according to claim 1, wherein the processing circuit is further configured to, in response to detecting a urination event by detecting that the urine sensitive circuit has been exposed to urine, record said data in a data structure linking the at least one parameter as determined by the measurement circuit, the estimated movement and/or posture and the estimate of the amount of urine released on to the urine sensitive circuit to the detected urination event.

12. The system according to claim 11, wherein the processing circuit is configured to store said data in an array data structure or as entries in a database.

13. The system according to claim 1, wherein the processing circuit is further configured to characterize a type of movement as movement by walking, by running, or by the user changing orientation or posture.

14. The system according to claim 1, wherein the measurement circuit is configured to measure an impedance of the urine bladder or perform an ultrasound measurement of a dimension of the urine bladder.

15. A system for monitoring incontinence for a user comprising:
a urine sensitive circuit configured to present a changed electrical characteristic when exposed to urine, wherein the changed electrical characteristic of the urine sensitive circuit is indicative of an amount of urine released on to the urine sensitive circuit;
a sensor configured to be attached on the user and determine an orientation and/or a movement of the sensor; and
a processing circuit configured to:
determine whether the urine sensitive circuit has been exposed to urine,
estimate the amount of urine released on to the urine sensitive circuit, and
in response to determining that the urine sensitive circuit has been exposed to urine, record data representing an estimated movement and/or posture of the user based on an orientation and/or a movement determined by the sensor, a parameter that influences a urine bladder fill level, and an estimate of the amount of urine released on to the urine sensitive circuit,
wherein the system further comprises a user interface or a receiver and wherein the parameter that influences the urine bladder fill level is a user-supplied parameter entered via the user interface or received by the receiver; or
wherein the system further comprises a timer and wherein the parameter that influences the urine bladder fill level is a measured parameter representing a time passed since a last toilet visit, or a time of day; or
wherein the system further comprises a temperature sensor and wherein the parameter that influences the urine bladder fill level is a measured parameter representing a temperature.

16. The system according to claim 15, wherein the user-supplied parameter is a volume of a fluid intake by the user, a type of fluid, a glomerular filtration rate (GFR), or a time of a last toilet visit.

17. The system according to claim 15, wherein the processing circuit is configured to calculate the urine bladder fill level based on the fluid intake of the user and a glomerular filtration rate (GFR).

18. The system according to claim 15, further comprising a measurement circuit configured to perform a measurement on a urine bladder of the user to determine at least one parameter which varies with a fill level of the urine bladder, and wherein the processing circuit, in response to determining that the urine sensitive circuit has been exposed to urine, is further configured to record data representing said at least one parameter determined by the measurement circuit.

19. The system according to claim 18, further comprising an underwear or undergarment wherein the urine sensitive circuit is configured to be positioned in connection to the underwear or undergarment, wherein the measurement circuit is configured to be secured to an edge of the underwear or undergarment and to be positioned at or near a bladder region of the user, and wherein the sensor is configured in a same unit as the measurement circuit.

20. The system according to claim 18, wherein the measurement circuit is configured to measure an impedance of the urine bladder or perform an ultrasound measurement of a dimension of the urine bladder.

* * * * *